(12) United States Patent
Ishibashi et al.

(10) Patent No.: US 10,925,798 B2
(45) Date of Patent: Feb. 23, 2021

(54) MOVABLE APPARATUS, MOVABLE SHEET, AND METHOD OF MANUFACTURING MOVABLE APPARATUS

(71) Applicant: SONY CORPORATION, Tokyo (JP)

(72) Inventors: Hidenori Ishibashi, Tokyo (JP); Fujio Kobayashi, Kanagawa (JP); Tomomasa Mizuno, Kanagawa (JP); Kazuhiro Kato, Tokyo (JP)

(73) Assignee: SONY CORPORATION, Tokyo (JP)

( * ) Notice: Subject to any disclaimer, the term of this patent is extended or adjusted under 35 U.S.C. 154(b) by 929 days.

(21) Appl. No.: 15/328,627

(22) PCT Filed: Jun. 9, 2015

(86) PCT No.: PCT/JP2015/002878
§ 371 (c)(1),
(2) Date: Jan. 24, 2017

(87) PCT Pub. No.: WO2016/021098
PCT Pub. Date: Feb. 11, 2016

(65) Prior Publication Data
US 2017/0209329 A1    Jul. 27, 2017

(30) Foreign Application Priority Data

Aug. 4, 2014 (JP) .................................. 2014-158408

(51) Int. Cl.
*A61H 3/00* (2006.01)
*F16C 11/06* (2006.01)
(Continued)

(52) U.S. Cl.
CPC ............... *A61H 3/00* (2013.01); *A61H 1/008* (2013.01); *F16C 11/06* (2013.01);
(Continued)

(58) Field of Classification Search
CPC ..... Y10T 403/32557; Y10T 403/32565; Y10T 403/32573; Y10T 403/32581;
(Continued)

(56) References Cited

U.S. PATENT DOCUMENTS 3,638,243 A * 2/1972 Campbell, Jr. ........ A61F 2/3804
   623/20.22
4,712,814 A * 12/1987 Petterson ............ F16C 11/0619
   285/325

(Continued)

FOREIGN PATENT DOCUMENTS

GB   1 321 342   *  6/1973   ............... A61F 1/24
GB   2 496 582   *  5/2013   ............... F16C 11/06
(Continued)

*Primary Examiner* — Michael P Ferguson
(74) *Attorney, Agent, or Firm* — Chip Law Group

(57) ABSTRACT

The movable apparatus includes a holding body and a movable body. The holding body includes a first opening portion and an internal space, and is constituted of one part. The movable body includes an internal body and a first movable shaft portion. The internal body is stored in the internal space of the holding body, and has such a size that the internal body is prevented from exiting the first opening portion even if the first opening portion is elastically deformed. The first movable shaft portion is capable of being moved integrally with the internal body, and is exposed to outside of the holding body from inside of the holding body through the first opening portion.

4 Claims, 9 Drawing Sheets

(51) Int. Cl.
*A61H 1/00* (2006.01)
*A61F 5/01* (2006.01)
*F16C 11/04* (2006.01)
*B25J 9/00* (2006.01)

(52) U.S. Cl.
CPC ...... *F16C 11/0604* (2013.01); *F16C 11/0614* (2013.01); *F16C 11/0623* (2013.01); *A61F 5/0118* (2013.01); *A61H 2205/06* (2013.01); *A61H 2205/10* (2013.01); *B25J 9/0006* (2013.01); *F16C 11/04* (2013.01); *F16C 11/0657* (2013.01)

(58) Field of Classification Search
CPC ..... Y10T 403/32549; Y10T 403/32591; F16C 11/0619; F16C 11/0604; A61H 3/00
See application file for complete search history.

(56) References Cited

U.S. PATENT DOCUMENTS

| | | | | |
|---|---|---|---|---|
| 5,035,464 A | * | 7/1991 | Spallholtz | A47C 7/62 297/144 |
| 6,454,808 B1 | * | 9/2002 | Masada | A61F 2/4241 623/21.15 |
| 6,758,622 B2 | * | 7/2004 | Burton | B60Q 1/0683 403/122 |
| 7,384,209 B2 | * | 6/2008 | Muders | F16C 11/0614 248/288.31 |
| 8,602,674 B2 | * | 12/2013 | Loewe | F16C 11/12 403/135 |
| 2008/0199248 A1 | | 8/2008 | Muders et al. | |
| 2010/0094185 A1 | * | 4/2010 | Amundson | A61F 5/0102 602/16 |

FOREIGN PATENT DOCUMENTS

| | | |
|---|---|---|
| JP | 43-024104 Y1 | 10/1968 |
| JP | 54-005974 U | 7/1980 |
| JP | 59-051955 U | 10/1985 |
| JP | 62-292915 A | 12/1987 |
| JP | 61-106504 U | 1/1988 |
| JP | 2004-523416 A | 8/2004 |
| JP | 2006-087478 A | 4/2006 |
| JP | 2010-131372 A | 6/2010 |
| JP | 2014-032097 A | 2/2014 |

* cited by examiner

MOVABLE APPARATUS, MOVABLE SHEET, AND METHOD OF MANUFACTURING MOVABLE APPARATUS

CROSS REFERENCE TO RELATED APPLICATIONS

This application is a U.S. National Phase of International Patent Application No. PCT/JP2015/002878 filed on Jun. 9, 2015, which claims priority benefit of Japanese Patent Application No. JP 2014-158408 filed in the Japan Patent Office on Aug. 4, 2014. Each of the above-referenced applications is hereby incorporated herein by reference in its entirety.

TECHNICAL FIELD

The present technology relates to a movable apparatus, a movable sheet, and a method of manufacturing a movable apparatus that achieve joints of a human body and other movable structures.

BACKGROUND ART

In related art, there has been proposed an apparatus that aids walking of a user by being attached to a thigh portion of the user and assisting motions of a hip joint and a knee joint (see, Patent Literature 1).

Patent Literature 2 discloses a walking aiding apparatus provided with an ankle joint portion. The ankle joint portion is provided with a spherical joint. The spherical joint is constituted of, for example, a joint shaft member, a spherical body provided on an end portion of the joint shaft member, and a holding portion that holds the spherical body in a freely swingable manner (see, for example, paragraph [0025] in Patent Literature 2).

CITATION LIST

Patent Literature

Patent Literature 1: Japanese Patent Application Laid-open No. 2006-087478
Patent Literature 2: Japanese Patent Application Laid-open No. 2010-131372

DISCLOSURE OF INVENTION

Technical Problem

The mechanism that constitutes the joint portions or the like in related art, for example, the spherical joint or the like mentioned above achieves such a structure that a great number of parts are combined to prevent a certain member from being detached from the other members, for example. This results in an increase in number of parts.

It is an object of the present technology to provide a movable apparatus, a movable sheet, and a method of manufacturing a movable apparatus that achieve a movable structure with a small number of parts.

Solution to Problem

To achieve the object mentioned above, a movable apparatus according to an embodiment of the present technology includes a holding body and a movable body.

The holding body includes a first opening portion and an internal space, and is constituted of one part.

The movable body includes an internal body and a first movable shaft portion. The internal body is stored in the internal space of the holding body, and the internal body has such a size that the internal body is prevented from exiting the first opening portion even if the first opening portion is elastically deformed. The first movable shaft portion is capable of being moved integrally with the internal body, and the first movable shaft portion is exposed to outside of the holding body from inside of the holding body through the first opening portion.

In the movable apparatus, the holding body is constituted of the one part and has the structure in which the internal body of the movable body does not exit the opening portion, if an elastic deformation of the opening portion (first opening portion) of the holding body is caused, with the result that it is possible to achieve the movable structure with a smaller number of parts. Further, the degree of freedom of rotation around the movable shaft portion (first movable shaft portion) is provided, so the movable shaft portion can be rotated.

The first opening portion may have an opening diameter larger than a diameter of a shaft member that constitutes the first movable shaft portion.

As a result, the first movable shaft portion can be freely moved in the opening portion, so a universal joint can be achieved. Further, for example, the first movable shaft portion can be rotated at the degree of freedom of 360° rotation around the first movable shaft portion.

The first opening portion is a guide long hole that guides the first movable shaft portion to move in one direction.

As a result, the first movable shaft portion can be moved in one direction, so various movements can be achieved with the rotational movement around the first movable shaft portion.

The holding body may further include a second opening portion, and the movable body may further include a second movable shaft portion provided to be movable integrally with the internal body and exposed to outside of the holding body through the second opening portion.

As a result, it is possible to achieve various movements by using the first and second movable shaft portions.

The first opening portion may be a first guide long hole that guides the first movable shaft portion to move in one direction. The second opening portion may be a second guide long hole that guides the second movable shaft portion to move in the one direction.

As a result, the second movable shaft portion and the second guide long hole function as a stopper that restricts the first movable shaft portion to axially rotate therearound. In a similar way, the first movable shaft portion and the first guide long hole function as a stopper that restricts the second movable shaft portion to axially rotate therearound.

The first opening portion may be a first guide long hole that guides the first movable shaft portion to move in one direction. Further, the second opening portion may be a second guide long hole that guides the second movable shaft portion to move in two directions including the one direction.

The first opening portion may have an opening diameter larger than a diameter of a shaft member that constitutes the first movable shaft portion.

The second opening portion may be a guide long hole that guides the second movable shaft portion to move in one direction.

As a result, in the state in which the movable apparatus includes the first movable shaft portion, the second movable shaft portion can be moved in the one direction, and can be moved rotationally around the second movable shaft portion.

The holding body may have a shape elongated in an axial direction of the first movable shaft portion.

As a result, the first movable shaft portion can be reciprocated in the shaft direction.

The movable apparatus may further include a power source that provides power to the movable body.

As a result, the power source can move the movable body, leading to expansion of the range of applications of the movable apparatus.

The power source may be disposed in the holding body.

As a result, the movable apparatus can be downsized.

The movable apparatus may further include a tension generation member disposed between the holding body and the movable body.

As a result, it is possible to position the holding body and the movable body.

In the movable apparatus, the power source may provide power to the tension generation member.

According to another embodiment of the present technology, there is provided a movable sheet including a plurality of movable apparatuses arranged and connected with each other. The plurality of movable apparatuses each has the features of the movable apparatus described above.

According to another embodiment of the present technology, there is provided a method of manufacturing the movable apparatus including reading 3D data of at least the holding body of the movable apparatus.

On the basis of the read 3D data, the holding body is formed by using a 3D printing technology to store the internal body of the movable body.

The use of the 3D printing technology downsizes the movable apparatus and eliminates an assembly operation.

Effects of the Invention

As described above, according to the present technology, it is possible to achieve the movable structure with a small number of parts.

It should be noted that, the effects described herein are not necessarily limited, any effect described in this disclosure may be obtained.

MODE(S) FOR CARRYING OUT THE INVENTION

Hereinafter, embodiments of the present technology will be described with reference to the drawings. A movable apparatus to be described below is applied to joint portions of a humanoid robot and an industrial robot, a motion assistance apparatus or the like that aids and assists motions of a human body, for example. However, the movable apparatus according to the present technology is not of course limited to those, and is applied to electronic apparatuses, tools, playthings provided with various movable structures, or other devices or objects.

First Embodiment

Figure 1:
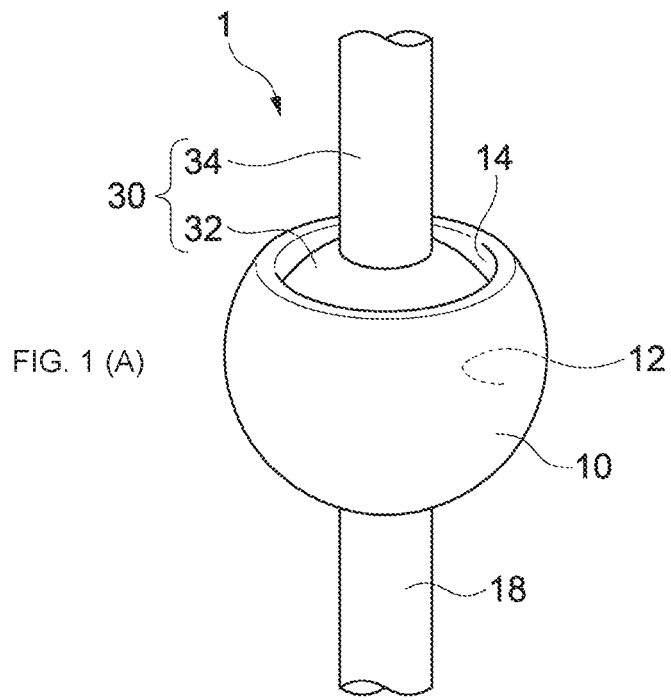
FIG. 1A is a perspective view showing a movable apparatus according to a first embodiment of the present technology.
FIG. 1B is a cross-sectional view in a vertical direction thereof.
Figure 1:
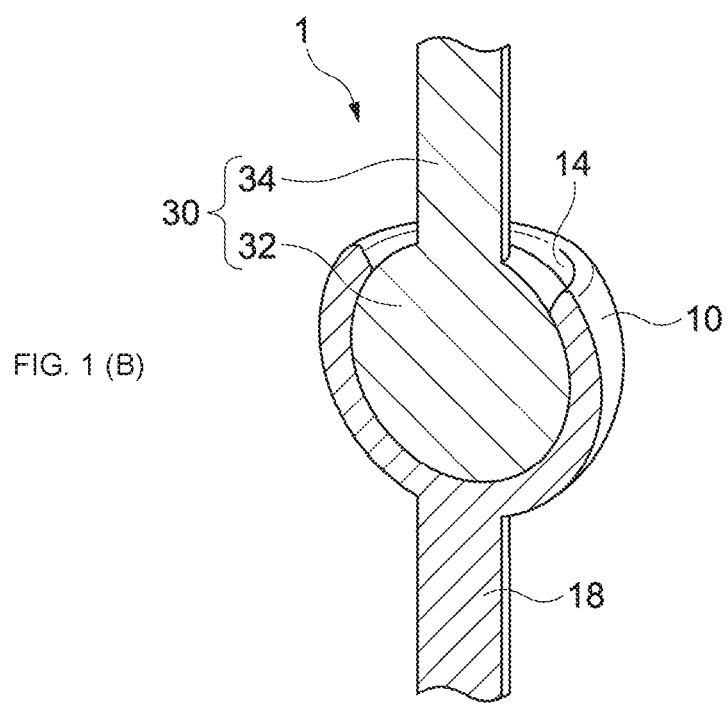

FIG. 1A is a perspective view showing a movable apparatus according to a first embodiment of the present technology. FIG. 1B is a cross-sectional view in a vertical direction thereof. A movable apparatus 1 is provided with a socket 10 including a function as a holding body and a movable body 30.

The socket 10 has an opening portion 14 (first opening portion) and an internal space 12 and is constituted of one part. The one part in this case means that the part is not constituted of two or more connected parts physically distanced. The movable body 30 has a spherical ball 32 as an internal body stored in the internal space 12 of the socket 10 and a movable shaft portion 34 that is movable integrally with the ball 32.

The ball 32 and the movable shaft portion 34 are integrally made of the same material, for example. The internal space 12 of the socket 10 is spherically formed. The ball 32 is stored in the socket 10 so as to be movable with a narrow gap between an inside surface of the socket 10 and the surface of the ball 32. The movable shaft portion 34 is formed into a long stick shape, for example, and is exposed to the outside of the socket 10 from the socket 10 through the opening portion 14.

An outline of the socket 10 is a part of the sphere but is not limited to this. Any shape can be used therefor. On a side of the socket 10 opposite to the opening portion 14, a connection portion 18 is provided. The socket 10 and the connection portion 18 are integrally made of the same material, for example. The connection portion 18 is also formed into a stick shape like the movable shaft portion 34, for example. The movable shaft portion 34 and the connection portion 18 can be connected to another member (mechanism, assembly, or device) (not shown).

The shape of the opening portion 14 is a circular shape when viewed in an axial direction of the movable shaft portion 34. An opening dimension of the opening portion 14 of the socket 10 is formed to be larger than a diameter (diameter of cross section) of the movable shaft portion 34. Further, the size of the ball 32 is set in such a manner that the ball 32 does not exit the opening portion 14 even if the opening portion 14 is elastically deformed. The deformation in this case is the elastic deformation as mentioned above and does not include plastic deformation. Of course, it is desirable that the rigidities of the socket 10 and the ball 32 be as high as possible. The shapes, lengths, diameters (diameters of cross sections), or the like of the movable shaft portion 34 and the connection portion 18 can be changed by designing as appropriate.

With the configuration as described above, in the movable body 30, the movable shaft portion 34 can be moved within the range of the opening portion 14, with the result that a universal joint can be achieved. Further, the ball 32 can be rotated around the movable shaft portion 34 in the socket 10, so the movable apparatus can obtain a rotational degree of freedom around one shaft.

The movable apparatus 1 is manufactured by a 3D (Dimension) printing technology. A 3D printer reads 3D data of the movable apparatus 1 and forms the movable apparatus 1 on the basis of the read 3D data. Specifically, after the 3D printer (not shown) forms the movable body 30, the movable body 30 is supported by an arbitrary supporting method, and the 3D printer can form the socket 10 that stores the ball 32 of the movable body 30. For example, the 3D printer supports the movable shaft portion 34 by suspending the movable shaft portion 34 from above in such a manner that the movable shaft portion 34 is disposed above the ball 32. Examples of the material of the movable apparatus 1 include photo-curable resin and metal powders.

As the 3D printer, for example, it is possible to use apparatuses disclosed in Japanese Patent Application Laid-open Nos. 2012-040757, 2012-106437, 2012-240216, 2013-207060, 2013-059983, or the like. The 3D printer that uses the one-dimensional liquid-level restriction method can cure a material by light irradiation in all directions in all postures, and therefore can form the movable apparatus.

Alternatively, not the whole movable apparatus 1 but at least the holding body (socket 10) may be formed by the 3D printing technology. In this case, for example, the 3D printer may form the socket 10 in such a manner that the movable body 30 is manufactured by a known technology other than the 3D printing technology, and then the ball 32 is stored. In this case, the material of the movable body 30 is not limited and an arbitrary material is used. Further, in this case, it is sufficient that the movable body 30 has the movable shaft portion 34 and the ball 32 as separated parts with those connected with each other.

As described above, the socket 10 is configured by one part and has the structure in which the ball 32 of the movable body 30 does not exit therefrom, with the result that it is possible to achieve the movable structure with the smaller number of parts, for example, two parts. In related art, at least three parts are necessary for the universal joint.

Further, in this embodiment, by using the 3D printing technology, it is possible to achieve the lightweight movable structure having the same intensity as before and having a smaller or the same size as before. Further, the 3D printer manufactures the movable apparatus 1, so an assembly operation is unnecessary.

It should be noted that, the connection portion 18 is the part integrally formed with the socket 10, so the structure including the connection portion 18 and the socket 10 can also be interpreted as the "holding body". That is, the holding body only has to have at least the opening portion 14 and the internal space 12 for storing the ball 32, which is an internal body, and is formed in an arbitrary shape. An outer shape thereof may be a semispherical or quarter-spherical shape. Alternatively, the outer shape thereof does not have to be a spherical part, that is, may be a cube, a rectangular parallelepiped, or a part thereof. This holds true for the second and subsequent embodiments.

Second Embodiment

Subsequently, a description will be given on a movable apparatus according to a second embodiment of the present technology. In the following description, substantially the same members, functions, and the like as the movable apparatus 1 according to the embodiment shown in FIG. 1A and FIG. 1B or the like are denoted by the same reference numerals, and a description thereof will be simplified or omitted. Different points will be mainly described.

Figure 2:
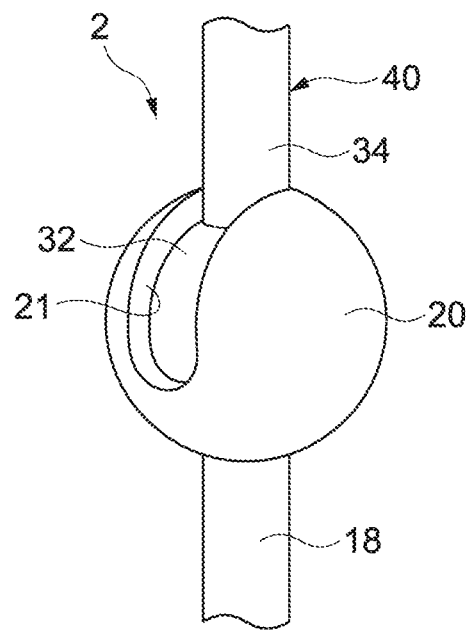
FIG. 2A is a perspective view showing a movable apparatus according to a second embodiment.
FIG. 2B is a perspective view showing a back surface side of the movable apparatus shown in FIG. 2A.
FIG. 2C is a cross-sectional view thereof.
Figure 2:
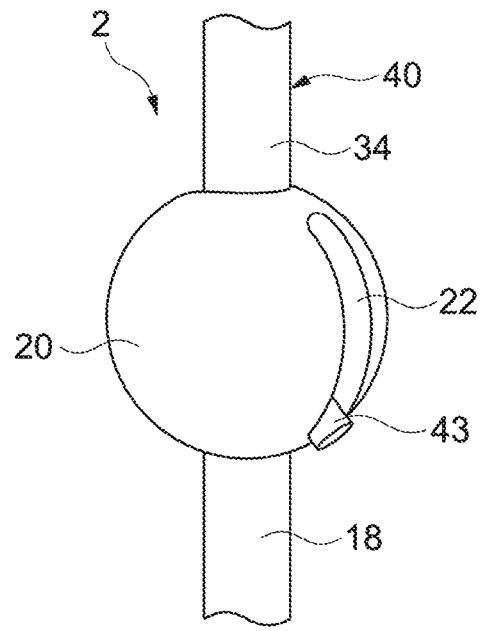
Figure 2:
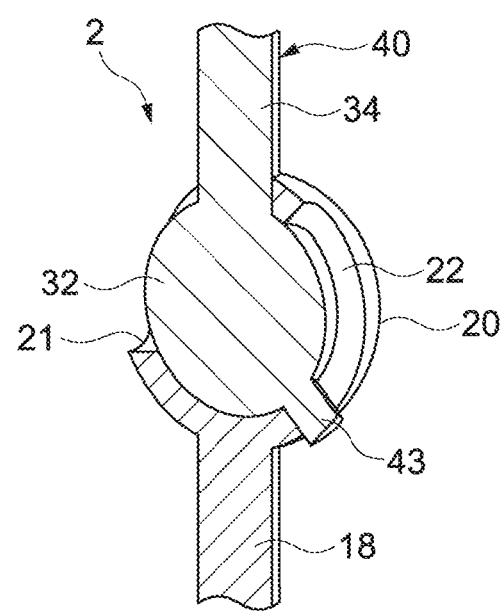

FIG. 2A is a perspective view showing a movable apparatus according to the second embodiment, and FIG. 2B is a perspective view showing a back surface side of the movable apparatus 2 shown in FIG. 2A. FIG. 2C is a cross-sectional view thereof. A socket 20, which is a holding body of the movable apparatus 2 according to this embodiment is configured by one part as in the first embodiment. Further, similarly, at least the socket 20 in the movable apparatus 2 is formed by the 3D printing technology.

The socket 20 has two opening portions, that is, a first opening portion 21 and a second opening portion 22. The first opening portion 21 is a guide long hole (first guide long hole) that guides one-directional movement (reciprocation movement) of the first movable shaft portion 34. That is, the first movable shaft portion 34 is rotatable by a predetermined angle in one plane. The first opening portion 21 is formed to have such a length that the degree of freedom of 90° rotational movement of the first movable shaft portion 34 is given to the first movable shaft portion 34.

To the ball 32 in the socket 20, the first movable shaft portion 34 and a stopper piece 43 (second movable shaft portion) are provided. The stopper piece 43 is provided so as to be movable integrally with the ball 32 while being exposed to the outside of the socket 20 through a second opening portion (second guide long hole) 22. The second opening portion 22 is a guide long hole that guides the movement of the stopper piece 43 and is formed along the same direction as the first opening portion 21. The length of the second opening portion 22 is substantially the same as the first opening portion 21. That is, the second opening portion 22 is formed to have such a length that the degree of freedom of 90° rotational movement of the stopper piece 43 is given to the stopper piece 43.

It should be noted that a width of the stopper piece 43 is shorter than that of the first movable shaft portion 34. Correspondingly, an opening area of the second opening portion 22 is formed to be smaller than that of the first opening portion 21.

With this structure, the stopper piece 43 and the second opening portion 22 have the function as a stopper that restricts an axial rotation of the first movable shaft portion 34.

Third Embodiment

Figure 3:
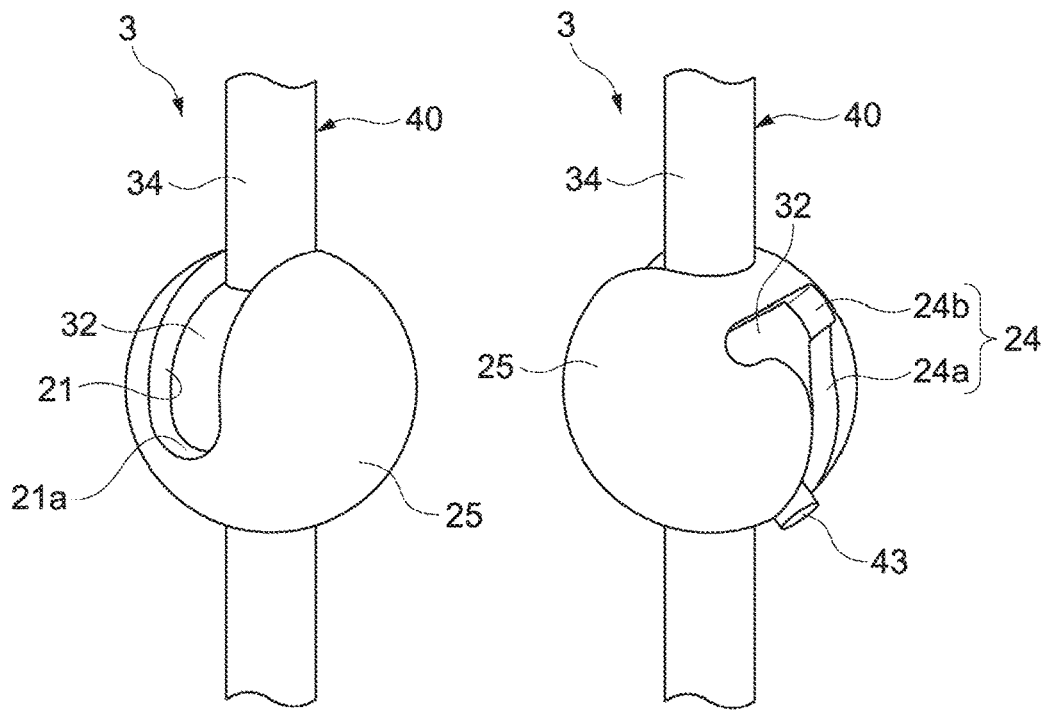
FIG. 3A is a perspective view showing a movable apparatus according to a third embodiment of the present technology.
FIG. 3B is a perspective view showing a back surface side of the movable apparatus shown in FIG. 3A.

FIG. 3A is a perspective view showing a movable apparatus 3 according to a third embodiment of the present technology, and FIG. 3B is a perspective view showing the movable apparatus 3 shown in FIG. 3A. The movable apparatus 3 in this embodiment is different from the movable apparatus 2 according to the second embodiment in terms of the degree of freedom of the movement of the stopper piece 43 (second movable shaft portion 34) having the stopper function.

That is, a second opening portion 24 formed as the second guide long hole in a socket 25 guides the stopper piece 43 to move in two directions including the one direction of the first movable shaft portion 34. Specifically, the second opening portion 24 is formed into a substantially T-letter shape. A one direction portion 24a of the second opening portion 24 coincides with one direction of the movement of the first movable shaft portion 34, and a different direction portion 24b is perpendicular thereto, for example.

With the structure as described above, the degree of freedom of the one-directional movement of the first movable shaft portion 34 is ensured.

Further, with this structure, on one end 21a (lower end in FIG. 3A) of the first opening portion 21, the first movable shaft portion 34 is rotatable therearound by a predetermined angle. That is, when the first movable shaft portion 34 is positioned on the one end 21a of the first opening portion 21, the stopper piece 43 is disposed in the different direction portion 24b of the second opening portion 24, with the result that the first movable shaft portion 34 is rotatable.

It should be noted that, the length of first opening portion 21 and the lengths of the one direction portion 24a and the different direction portion 24b of the second opening portion 24 can be changed as appropriate. As a result, it is possible to change design within the range of the movement of the first movable shaft portion 34 and the range of the axial rotation angle therearound.

Modified Example of Third Embodiment

Figure 4:
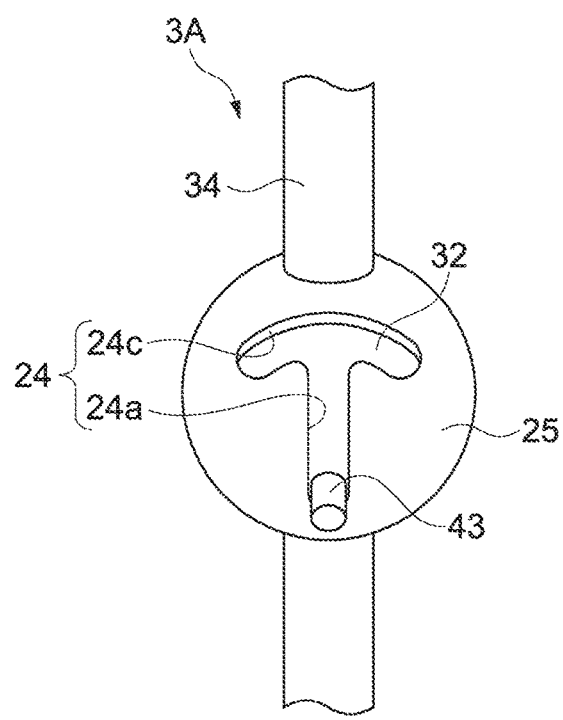
FIG. 4 is a diagram showing a modified example of the movable apparatus according to the third embodiment.

FIG. 4 is a diagram showing a modified example of the movable apparatus 3 according to the third embodiment. In the second embodiment, the different direction portion 24b of the second opening portion 24 is formed along a straight line, while in an example of a movable apparatus 3A, a different direction portion 24c is formed along an arc shape. As a result, at the position of the lower end of the first opening portion 21, the axial rotation of the first movable shaft portion 34 therearound is made to be smooth.

As a further another modified example of this embodiment, the first opening portion 21 may have a circular (another shape possible), large opening area like the opening portion 14 in the first embodiment. With this structure, the first movable shaft portion 34 also moves like that of the movable apparatus 3.

Fourth Embodiment

Figure 5:
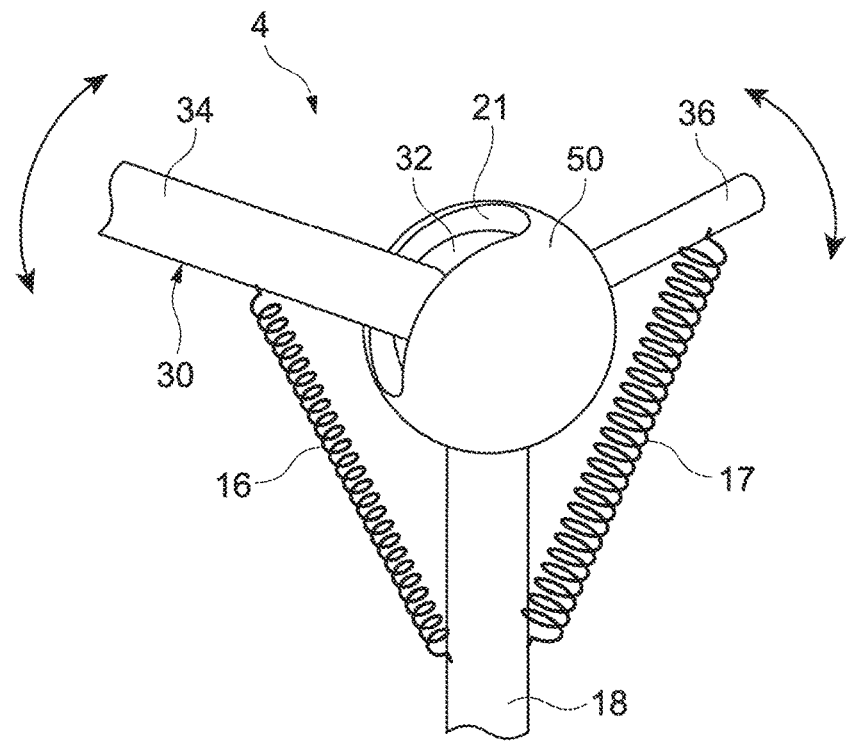
FIG. 5 is a perspective view showing a movable apparatus according to a fourth embodiment of the present technology.

FIG. 5 is a perspective view showing a movable apparatus 4 according to the fourth embodiment of the present technology. In the movable apparatus 4, a first spring 16, which is a first tension generation member is provided between the first movable shaft portion 34 and the connection portion 18 provided to a socket 50. The first movable shaft portion 34 is provided so as to be movable in one direction along the first opening portion (first guide long hole).

Although not shown, in the socket 50, formed is a second opening portion (second guide long hole) for causing a spring attachment portion 36 as the second movable shaft portion to move in one direction. Further, between the spring attachment portion 36 and the connection portion 18, a second spring 17, which is a second tension generation member is provided.

The first spring 16 and the second spring 17 mainly have a function for positioning the movable body 30. For example, in the state shown in FIG. 5, the tensions of the first spring 16 and the second spring 17 are balanced, the first movable shaft portion 34 (and spring attachment portion 36) is positioned. On the basis of spring constants and attachment positions of the first spring 16 and the second spring 17, the positioning thereof can be performed without causing the first movable shaft portion 34 to fall down due to gravity.

It should be noted that, to a tip end of the spring attachment portion 36, a driven portion is not attached. The spring attachment portion 36 mainly has a function of attaching the second spring 17 between the connection portion 18 and the spring attachment portion 36. However, the spring attachment portion 36 may function as the "second movable shaft portion" to a tip end of which a driven portion is attached.

Modified Example of Fourth Embodiment

Figure 6:
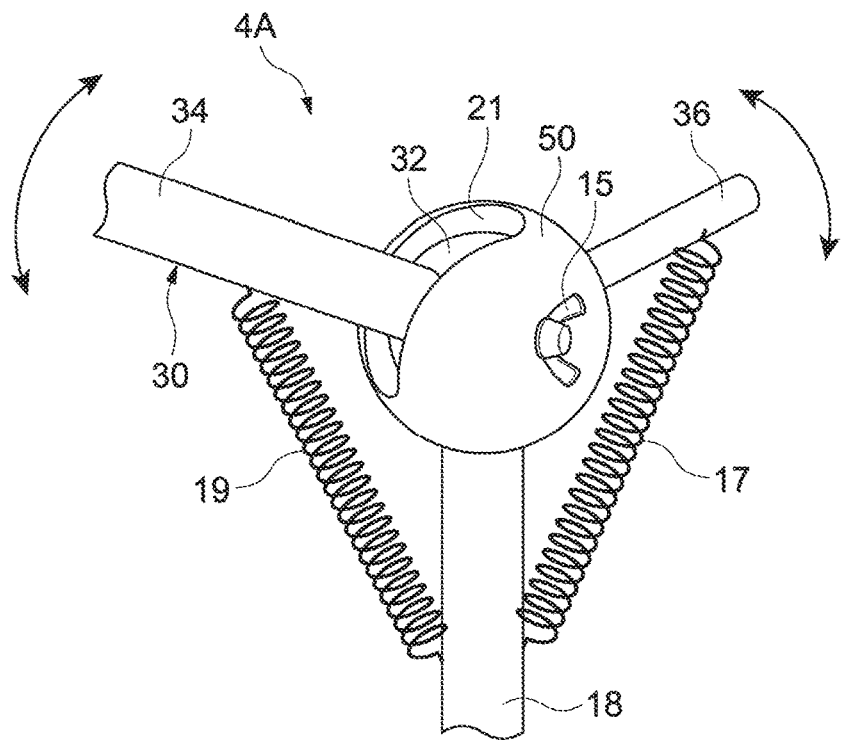
FIG. 6 is a diagram showing a modified example of the movable apparatus according to the fourth embodiment.

FIG. 6 is a diagram showing a modified example of the movable apparatus 4 according to the fourth embodiment. A spring constant of a first spring 19 of a movable apparatus 4A is larger than the spring constant of the first spring 16 in the fourth embodiment. In a side surface of the socket 50, a fixation bolt 15 is inserted, and the position of the ball 32 is fixed with the fixation bolt 15. In this way, even by the design of not balancing the tensions of the first spring 19 and the second spring 17 by the spring constants, it is possible to fix the movable body 30 in position with the fixation bolt 15.

Fifth Embodiment

Figure 7:
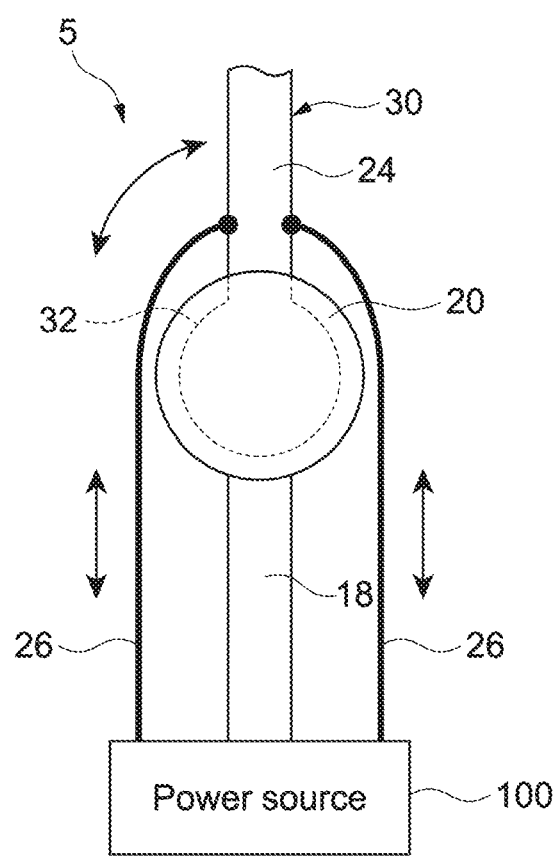
FIG. 7 is a schematic diagram showing a movable apparatus according to a fifth embodiment of the present technology.

FIG. 7 is a schematic diagram showing a movable apparatus according to a fifth embodiment of the present technology. A movable apparatus 5 is provided with the socket 20, the movable body 30, a power source 100, the connection portion 18, and wires 26, which is a tension generation member. The connection portion 18 connects the socket 20 and the power source 100. The wires 26 are disposed between the power source 100 and the movable body 30, and the number of wires is two or more, for example. The movable body 30 is configured so as to reciprocate within an arbitrary angle range (for example, 90° as shown in FIG. 2A, FIG. 2B, and FIG. 2C) in one direction indicated by the arrow in the figure, for example.

The power source 100 is configured by a motor, for example. To the wires 26, power is given by the power source 100, and the wires 26 are reeled out and reeled in by a reel (not shown) provided to the power source 100. The wires 26 are operated in the state in which tensions are given thereto along a guide (not shown).

The motor as the power source 100 may be a rotary motor or a linear motor. Alternatively, the power source 100 is not limited to the motor and may be a fluid pressure pump.

For example, the case where the movable apparatus 5 according to this embodiment is applied to a joint portion of an arm of a robot will be described. For the joint portion, when the power source 100 pulls one of the wires 26, a bending operation of the arm can be performed, and when the power source 100 pulls the other wire 26, an extending operation of the arm can be performed. The state of the movable apparatus 5 shown in FIG. 7 is the state in which the arm is extended. By controlling a length of the wires 26 pulled by the power source 100, a pulling force, and a pulling speed, various joint motions can be achieved. For example, in the case where the joint portion is used as a motion assistance apparatus for a human, in accordance with the state from when a user starts to perform a bending operation and an extending operation until the user stops the operations, the pulled length of the wires 26, the pulling force, and the pulling speed are controlled, with the result that optimal assistance operations can be provided to users.

In particular, by providing, to the movable apparatus 1 according to the first embodiment, the power source 100 and the wires 26 (spring 16, 17, or the like shown in FIG. 5 also possible) as in this embodiment, the following effect is exerted. For example, in bending and extending operations of a knee, not only a one-directional movement (rotation in one plane) of the movable shaft portion 34 but also a "twisting" operation by the rotation around the movable shaft can be performed. Thus, the movable apparatus 5 can achieve movements appropriate to a body.

Examples of the method of operating the movable apparatus 5 include a method in which myoelectric potentials are input in a motor driver and a method in which a user holds an operation unit (not shown) for operating the movable apparatus 5 and operates the same through the operation unit.

For example, the case where the movable apparatus 5 is applied to a joint portion of a motion assistance apparatus for a lower body of a user is considered. In this case, the operation unit is configured as a glove-shaped operation unit. When the user grasps the glove-shaped operation unit in the state in which the user sits down on a chair, the movable apparatus 5 performs the extending operation, with the result that an operation of standing up can be supported. Further, when the user opens the hand in the stand-up state, the movable apparatus 5 performs the bending operation, with the result that an operation of sitting down can be supported.

As described above, the movable apparatus 5 according to this embodiment can be used as the motion assistance apparatus, and can assist the user to stand up, sit down, walk, and run. The movable apparatus 5 can also support workers who require power, for example, such a task that a carer lifts a care receiver up or down in his/her arms in a caring place. Therefore, it is possible to prevent cares and care receivers from falling or being injured.

In the fifth embodiment, instead of the wires 26, a spring or a gear may be provided. The gear functions as a power transmission portion for transmitting the power of the power source 100 to the movable body 30.

Sixth Embodiment

Figure 8:
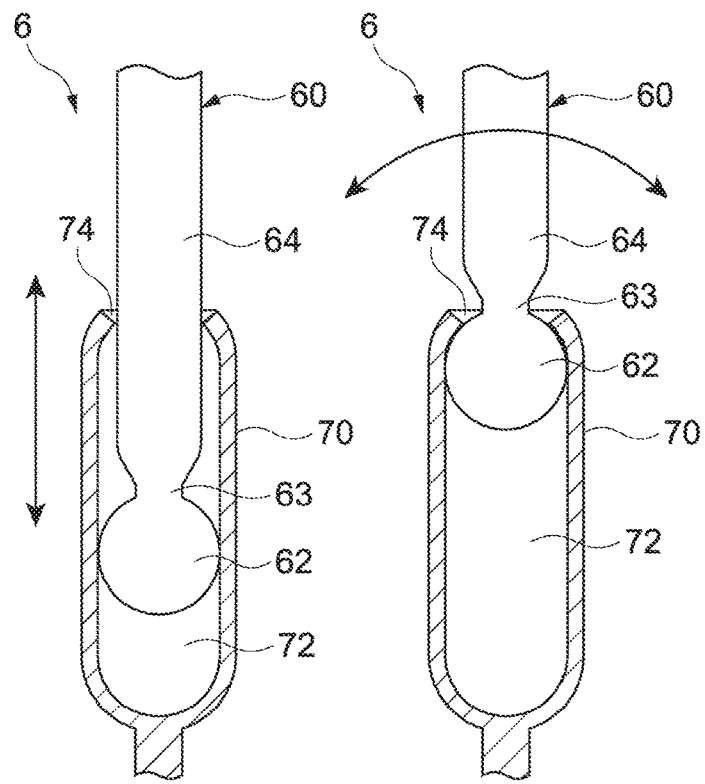
FIGS. 8A and 8B are cross-sectional views showing a movable apparatus according to a sixth embodiment of the present technology.

FIGS. 8A and 8B are cross-sectional views showing a movable apparatus according to a sixth embodiment of the present technology. The movable apparatus 6 is provided with a socket 70 having a substantially cylindrical shape. The socket 70 has a shape elongated in an axial direction of a movable shaft portion 64 of a movable body 60. On an end portion of the socket 70, an opening portion 74. On an end portion of the movable body 60, a ball 62 is provided. The sizes of the opening portion 74 and the ball 62 are designed in such a manner that the ball 62 does not exit the opening portion 74. As a result, the movable body 60 can linearly reciprocate in a direction of the arrow shown in FIG. 8A.

Further, the movable shaft portion 64 of the movable body 60 has a constricted portion 63 between the ball 62 and the movable shaft portion 64. A cross-sectional diameter of the constricted portion 63 is formed to be smaller than an opening diameter of the opening portion 74. With this configuration of the movable body 60, when the ball 62 is disposed on one end portion of the socket 70 as shown in FIG. 8B, a 3D free motion like the universal joint can be performed. Further, at this time, the movable shaft portion 64 can axially rotate therearound.

Seventh Embodiment

Figure 9:
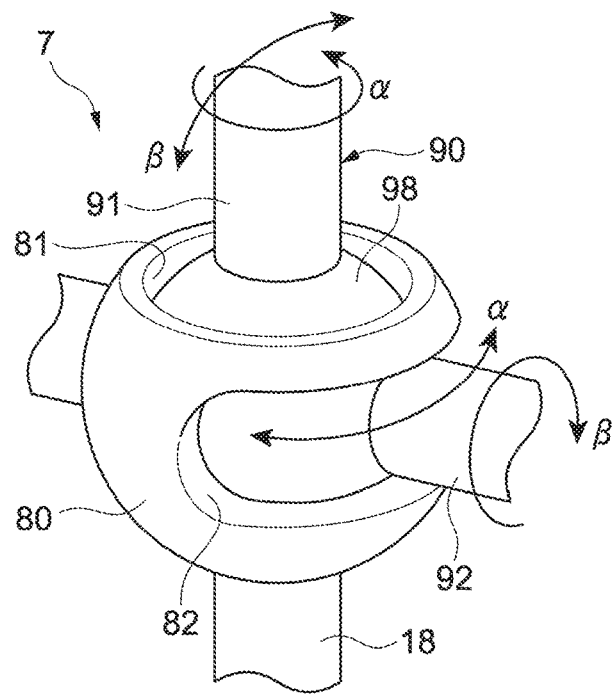
FIG. 9 is a perspective view showing a movable apparatus according to a seventh embodiment of the present technology.

FIG. 9 is a perspective view showing a movable apparatus according to a seventh embodiment of the present technology. A socket 80 of a movable apparatus 7 has a first opening portion 81 and a second opening portion 82, which is a guide long hole that causes a second movable shaft portion 92 of a movable body 90 to move in one direction. For example, a first movable shaft portion 91 and the second movable shaft portion 92 are orthogonal to each other.

The first movable shaft portion 91 of the movable body 90 is axially rotated within a movement range of the second movable shaft portion 92 guided in one direction by the second opening portion 82 around the first movable shaft portion 91 (rotated in the direction indicated by the arrow α shown in the figure). Further, the first movable shaft portion 91 can be rotated in a direction in which the second movable shaft portion 92 is rotated therearound (rotated in a direction indicated by the arrow β shown in the figure).

Figure 10:
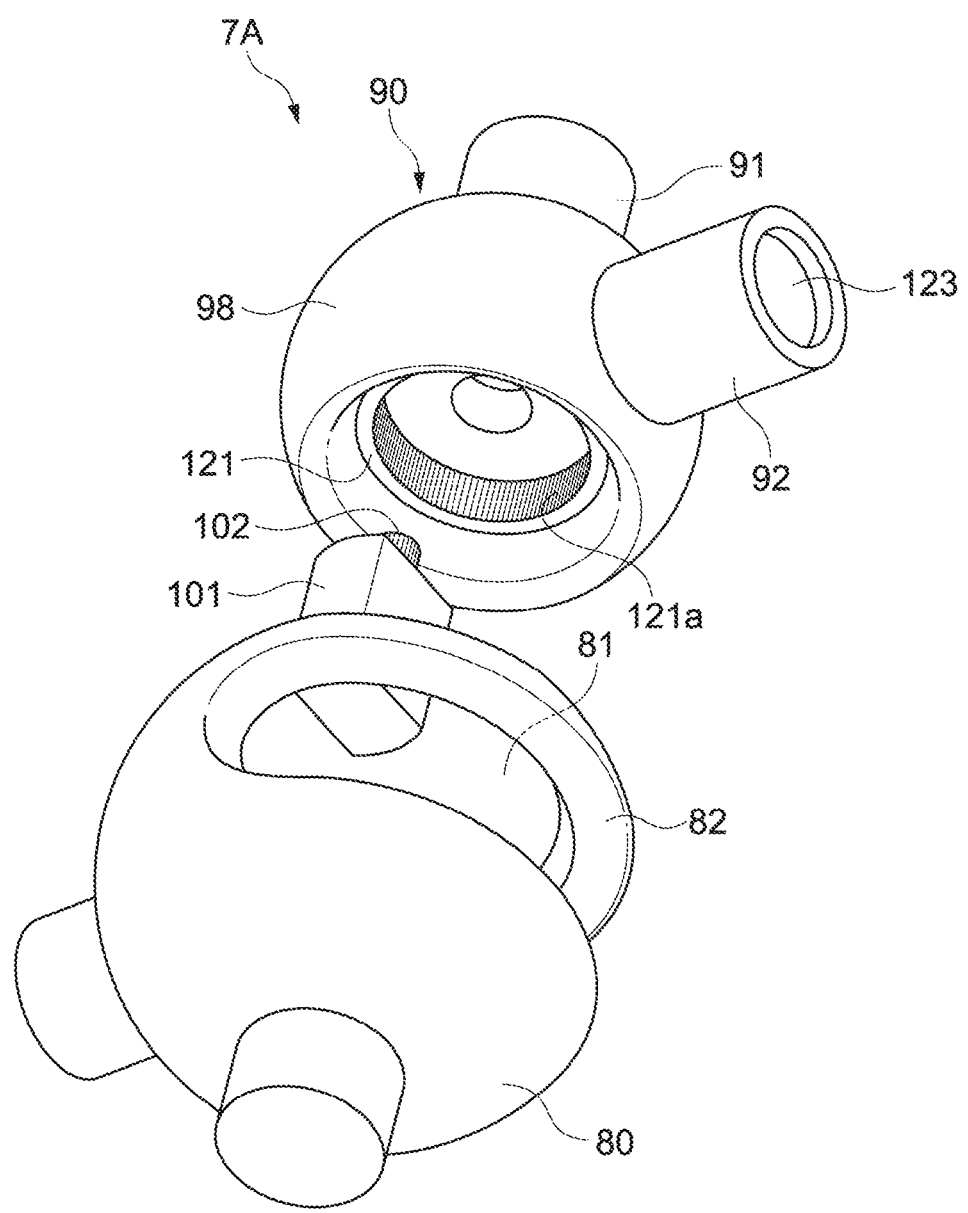
FIG. 10 is an exploded view showing a movable apparatus having a form in which a motor is disposed in a socket of the movable apparatus shown in FIG. 9.

FIG. 10 is an exploded view showing a movable apparatus 7A having the structure in which a motor 101 as the power source is disposed in the socket 80 of the movable apparatus 7 shown in FIG. 9. The motor 101 drives the movable body 90 in the rotation direction indicated by the arrow α shown in FIG. 9. In the rotation direction indicated by the arrow β, the movable body 90 can obtain free movements.

Inside a ball 98 as an internal body of the movable body 90, a space is formed. In the space, the motor 101 is partially or entirely disposed, and a ring gear 121 rotated by the motor 101 is disposed. Specifically, for example, the motor 101 is disposed in the socket 80 in such a manner that a gear 102 attached to an output shaft of the motor 101 is engaged with teeth 121a provided inside the ring gear 121. The motor 101 is connected to the socket 80, for example.

To the ring gear 121, an attachment shaft portion 123 extended in a vertical direction is provided. The attachment shaft portion 123 is stored in the second movable shaft portion 92 so as to be rotatable (rotatable in the direction indicated by the arrow β shown in FIG. 9). The ring gear 121 and the attachment shaft portion 123 are integrally formed. As a result, the ring gear 121 is axially rotatable around the attachment shaft portion 123 and can be tilted with respect to the ball 98 in the space of the ball 98.

It should be noted that, in the case where the ball 98 is rotated in the direction indicated by the arrow β, the output shaft of the motor 101 can be moved in one direction corresponding to the tilt of the ball 98, or the motor 101 itself can move in one direction corresponding to the tilt of the ball 98 in the socket 80.

As described above, the motor 101 as the power source is disposed in the socket 80, so it is possible to downsize the movable apparatus 7A.

As a method of manufacturing the movable apparatus 7A according to this embodiment by using the 3D printing technology, the following example can be cited. For example, the movable body 90 is manufactured by an arbitrary method (by the 3D printing technology or by another method). The movable body 90 is equipped with the motor 101. Further, by the 3D printing technology, the socket 80 that stores the movable body 90 and the motor 101 only has to be formed.

Figure 11:
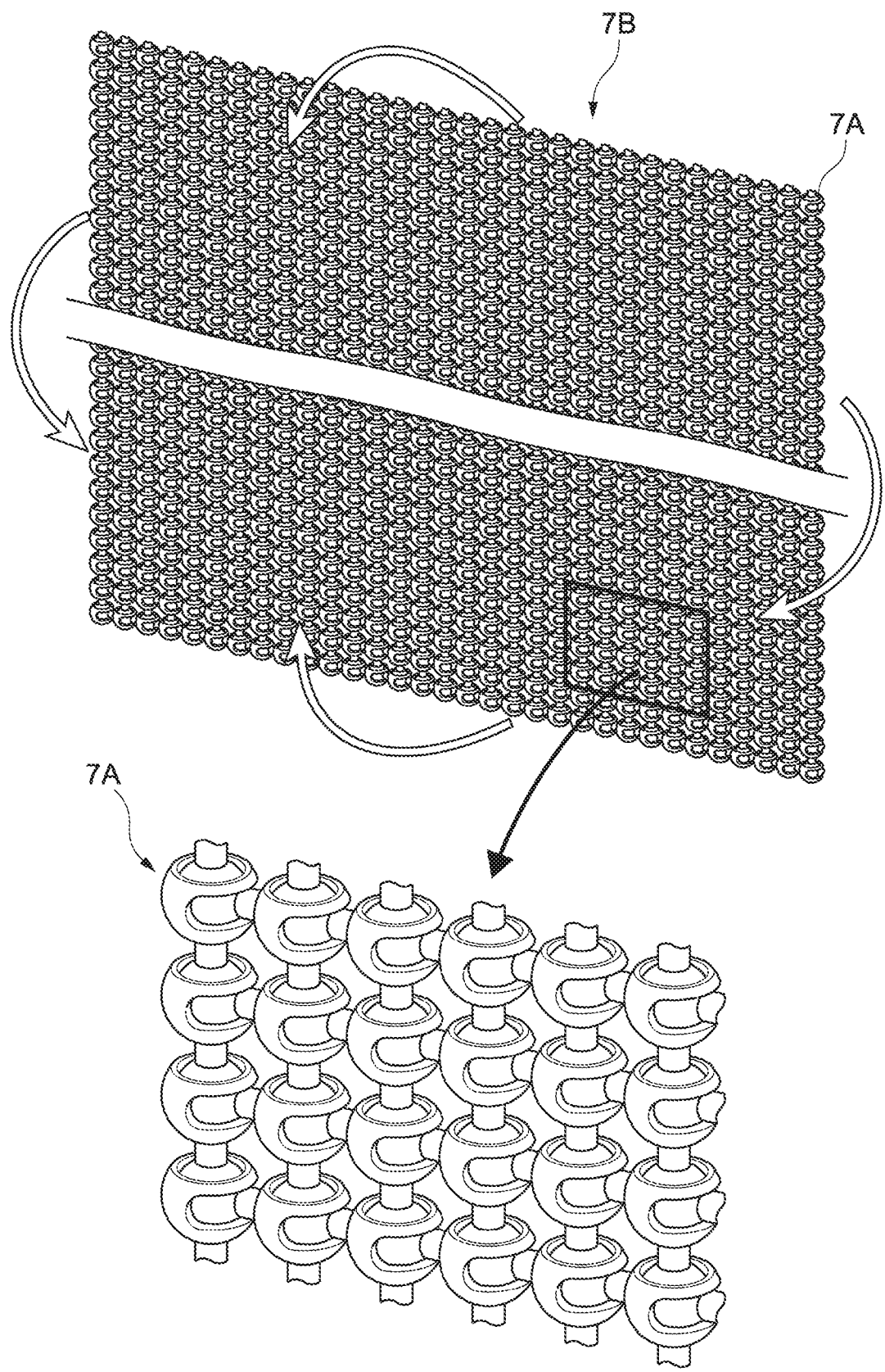
FIG. 11 is a perspective view showing a movable sheet constituted of a plurality of a movable apparatuses with the movable apparatus according to the seventh embodiment as a unit structure.

FIG. 11 is a perspective view showing a movable sheet configured by arranging a plurality of movable apparatuses 7A in a matrix pattern with the movable apparatus 7A according to the above embodiment as a unit configuration. The upper view of FIG. 11 shows the entire movable sheet, and the lower view of FIG. 11 shows partially enlarged view thereof. For example, the first connection portion 18 provided to the socket 80 shown in FIG. 9 is provided as the first movable shaft portion 91 for a different movable apparatus 7A adjacent thereto or is connected to the first movable shaft portion 91. Further, the second movable shaft portion 92 provided to the socket 80 shown in FIG. 9 is provided as the second movable shaft portion 92 for a different movable apparatus 7A adjacent thereto or is connected to the second movable shaft portion 92 of the different movable apparatus 7A.

In a movable sheet 7B thus obtained as described above, when the motor 101 drives the movable body 90 in a predetermined rotation direction (indicated by the arrow α shown in FIG. 9), the sheet can be moved so as to bend. Further, a user can freely move the movable sheet 7B in a different rotation direction (indicated by the arrow β shown in FIG. 9).

In particular, the movable sheet 7B is manufactured by the 3D printing technology and thus can be downsized. Therefore, various applications thereof can be expected.

Figure 12:
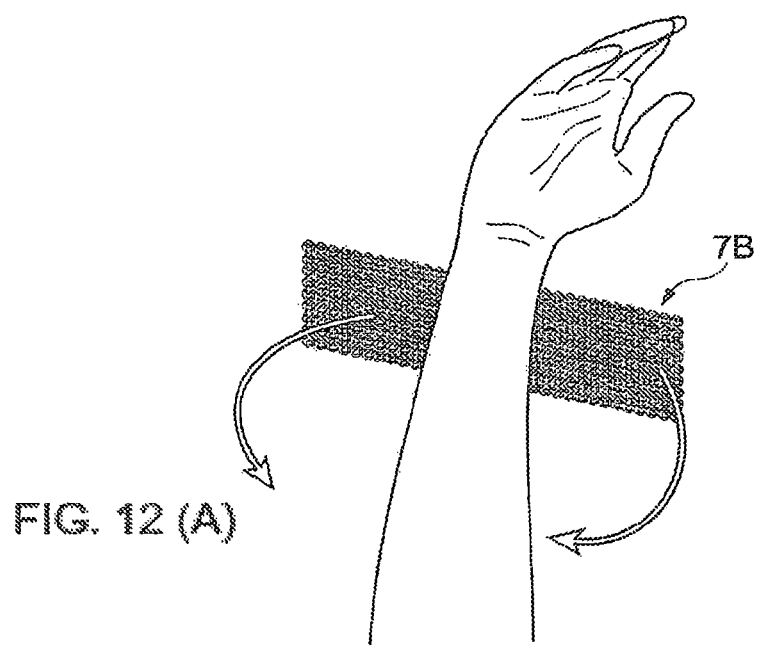
FIGS. 12A and 12B are diagrams for explaining an application example of the movable sheet shown in FIG. 11.
Figure 12:
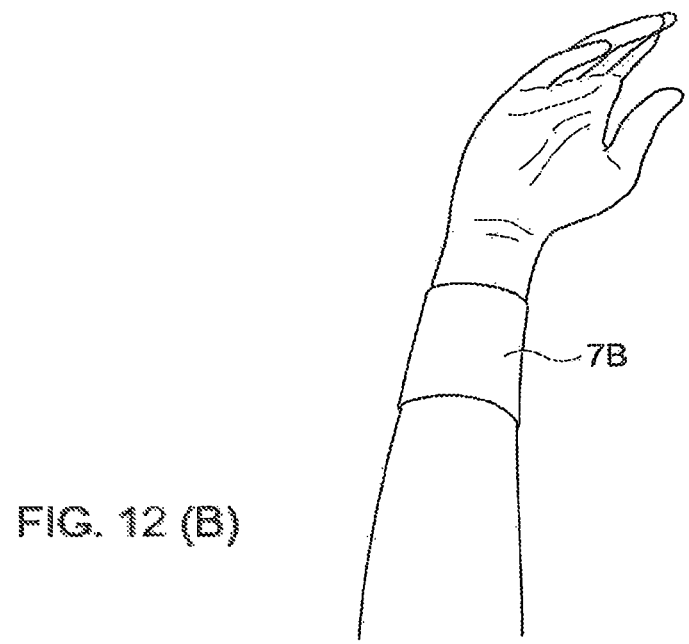

FIGS. 12A and 12B are diagrams for explaining an application example of the movable sheet 7B shown in FIG. 11. For example, the movable sheet 7B elongated in one direction is prepared, and a user wears the movable sheet 7B around an arm or a wrist to use the movable sheet as a wrist band. Alternatively, the movable sheet can be used as a band of a watch (not shown). By the drive of the motors 101 of the movable sheet 7B, the movable sheet 7B can be placed around the arm.

Alternatively, the movable sheet 7B can be used as a motion assistance apparatus for a user. In particular, as shown in FIGS. 12A and 12B, the movable sheet 7B having the downsized movable apparatuses 7A as the unit structure can be fitted tightly to a skin in use, so the movable sheet 7B exerts the function of a powered exoskeleton. The movable apparatuses 7A as the unit structure can be downsized, so a user can wear the movable sheet 7B under his/her clothes inconspicuously without feeling someone's eyes on the user.

Other Embodiments

The present technology is not limited to the above embodiments, and can achieve other various embodiments.

For example, in the movable apparatus 1 according to the first embodiment, the shape of the opening portion 14 of the socket 10 is a circle when viewed in the axial direction of the movable shaft portion 34, but may be an oval or a polygon. The same holds true for the seventh embodiment.

The socket according to each of the embodiments may be constituted of two or more parts. In this case, the socket is constituted of the holding body (element having at least an opening and an internal space) and one or more different parts attached to the holding body.

In the above embodiments, the ball, which is the internal body that moves in the socket, has a spherical shape or a partially spherical shape. However, the shape thereof is not limited to the spherical shape, and may be an ellipsoidal body, a polyhedron, a cylinder, a prismatic body, or a part thereof. However, the more spherical the shape of the internal body, the higher the degree of freedom of the movement becomes.

The movable apparatus 7 (7A) according to the seventh embodiment has the structure with the power source, but may not have the power source.

In the above embodiments, the second opening portion 22 and the like (see, for example, FIG. 2A, FIG. 2B, and FIG. 2C) are formed into the guide long hole shape. However, the first opening portion and the second opening portion may have openings each having a diameter larger than the cross-sectional diameter of the movable shaft portion like the opening portion 14 shown in FIG. 1A and FIG. 1B. As a result, a plurality of movable shaft portions can achieve the movement of the universal joint.

At least two of the features of the embodiments described above can be combined with each other.

For example, as indicated by the movable apparatus 7A (see, FIG. 10) in the example of the seventh embodiment, the structure in which the power source such as the motor 101 is disposed in the holding body can be applied to the different embodiments.

It should be noted that the present technology can take the following configurations.

(1) A movable apparatus, including:

a holding body including a first opening portion and an internal space, the holding body being constituted of one part; and a movable body including an internal body stored in the internal space of the holding body and a first movable shaft portion capable of being moved integrally with the internal body, the internal body having such a size that the internal body is prevented from exiting the first opening portion even if the first opening portion is elastically deformed, the first movable shaft portion being exposed to outside of the holding body from inside of the holding body through the first opening portion.

(2) The movable apparatus according to (1), in which the first opening portion has an opening diameter larger than a diameter of a shaft member that constitutes the first movable shaft portion.

(3) The movable apparatus according to (1), in which the first opening portion is a guide long hole that guides the first movable shaft portion to move in one direction.

(4) The movable apparatus according to (1), in which the holding body further includes a second opening portion, and the movable body further includes a second movable shaft portion provided to be movable integrally with the internal body and exposed to outside of the holding body through the second opening portion.

(5) The movable apparatus according to (4), in which the first opening portion is a first guide long hole that guides the first movable shaft portion to move in one direction, and the second opening portion is a second guide long hole that guides the second movable shaft portion to move in the one direction.

(6) The movable apparatus according to (4), in which the first opening portion is a first guide long hole that guides the first movable shaft portion to move in one direction, and the second opening portion is a second guide long hole that guides the second movable shaft portion to move in two directions including the one direction.

(7) The movable apparatus according to (4), in which the first opening portion has an opening diameter larger than a diameter of a shaft member that constitutes the first movable shaft portion.

(8) The movable apparatus according to (7), in which the second opening portion is a guide long hole that guides the second movable shaft portion to move in one direction.

(9) The movable apparatus according to any one of (1) to (8), in which the holding body has a shape elongated in an axial direction of the first movable shaft portion.

(10) The movable apparatus according to any one of (1) to (8), further including:

a power source that provides power to the movable body.

(11) The movable apparatus according to (10), in which the power source is disposed in the holding body.

(12) The movable apparatus according to (10), further including:

a tension generation member disposed between the holding body and the movable body.

(13) The movable apparatus according to (12), in which the power source provides power to the tension generation member.

(14) A movable sheet, including:

a plurality of movable apparatuses arranged and connected with each other, in which the plurality of movable apparatuses each includes a holding body including a first opening portion and an internal space, the holding body being constituted of one part, and a movable body including an internal body stored in the internal space of the holding body and a first movable shaft portion capable of being moved integrally with the internal body, the internal body having such a size that the internal body is prevented from exiting the first opening portion even if the first opening portion is elastically deformed, the first movable shaft portion being exposed to outside of the holding body from inside of the holding body through the first opening portion.

(15) A method of manufacturing a movable apparatus including a holding body including a first opening portion and an internal space, the holding body being constituted of one part, and a movable body including an internal body stored in the internal space of the holding body and a first movable shaft portion capable of being moved integrally with the internal body, the internal body having such a size that the internal body is prevented from exiting the first opening portion even if the first opening portion is elastically deformed, the first movable shaft portion being exposed to outside of the holding body from inside of the holding body through the first opening portion, the method including:

reading 3D data of at least the holding body of the movable apparatus; and forming, on the basis of the read 3D data, the holding body by using a 3D printing technology to store the internal body of the movable body.

REFERENCE SIGNS LIST 1, 2, 3, 3A, 4, 4A, 5, 6, 7, 7A movable apparatus
7B movable sheet
10, 20, 25, 50, 70, 80 socket
12 internal space
14, 74, 81 opening portion (first opening portion)
21 first opening portion
22, 24, 82 second opening portion
26 wire
30, 60, 90 movable body
32, 62, 98 ball (internal body)
34, 64, 91 movable shaft portion (first movable shaft portion)
36 attachment portion (second movable shaft portion)
43 stopper piece (second movable shaft portion)
92 second movable shaft portion
100 power source

The invention claimed is:

1. A movable apparatus comprising a pivot joint of a walking assistance or robotic exoskeleton, comprising:
 a first frame component comprising a holding body comprising:
  a socket housing having an internal cavity;
  a first opening comprising a first elongated guide slot radially-extending through a sidewall of the socket housing into the internal cavity;
  a second opening comprising a second elongated guide slot radially-extending through the sidewall of the socket housing, the first and second openings being circumferentially-spaced and aligned within a single plane; and
  a shaft-shaped connection member extending from the socket housing opposite the first and second openings and functioning as a frame component; and
 a second frame component comprising a movable body comprising:
  a spherical ball pivotably disposed within the internal cavity of the holding body socket housing;
  a first movable shaft extending from the spherical ball through the first opening and functioning as the frame component, movement of the first movable shaft within the first elongated guide slot limiting rotation of the spherical ball to a predetermined angle within a single plane; and
  a second movable shaft extending from the spherical ball through the second opening and functioning as a stopper, movement of the second movable shaft within the second elongated guide slot limiting rotation of the spherical ball to the predetermined angle within the single plane and preventing rotation of the spherical ball about an axis of the first moveable shaft,
 wherein the spherical ball is fully enclosed within internal cavity of the socket housing, and the socket housing is formed around the spherical ball as a single piece member by an addictive manufacturing process;
 a first spring coupled between the first movable shaft and the shaft-shaped connection member of the first frame component to bias a position of the first movable shaft to a desired position within the first opening; and
 a second spring coupled between the second movable shaft and the shaft-shaped connection member to balance a tension force of the first spring and to prevent the first movable shaft of the second frame component from falling due to gravity.

2. The movable apparatus according to claim 1, wherein:
a direction of the second opening is along a direction of the first opening, and
a length of the first opening is similar to a length of the second opening.

3. The movable apparatus according to claim 1, wherein a width of the second movable shaft is smaller than a width of the first movable shaft.

4. The movable apparatus according to claim 1, wherein a size of the second opening is smaller than a size of the first opening.

* * * * *